United States Patent [19]

Kumagai et al.

[11] Patent Number: 5,432,067
[45] Date of Patent: Jul. 11, 1995

[54] PROCESS FOR PRODUCTION OF BIOTIN USING BACTERIA BELONGING TO THE GENUS SPHINGOMONAS

[75] Inventors: Kazuo Kumagai, Sanda; Misao Miki, Minoo; Emiko Kawano, Osaka; Satoshi Mitsuda, Takarazuka, all of Japan

[73] Assignee: Sumitomo Chemical Company, Limited, Osaka, Japan

[21] Appl. No.: 111,440

[22] Filed: Aug. 25, 1993

[30] Foreign Application Priority Data

Sep. 10, 1992 [JP]  Japan ................. 4-241748

[51] Int. Cl.6 .............. C12P 1/04; C12P 11/18; C12N 1/12; C12N 1/20
[52] U.S. Cl. .................. 435/119; 435/170; 435/252.1; 435/822
[58] Field of Search ............ 435/253.3, 252.1, 874, 435/822, 170, 119

[56] References Cited

U.S. PATENT DOCUMENTS

| | | | |
|---|---|---|---|
| 3,393,129 | 7/1968 | Shibata et al. | 195/28 |
| 3,859,167 | 1/1975 | Ogino et al. | 195/51 R |
| 4,563,426 | 1/1986 | Yamada et al. | 435/119 |
| 5,179,011 | 1/1993 | Kishimoto et al. | 435/119 |
| 5,238,838 | 8/1993 | Kula et al. | 435/228 |

FOREIGN PATENT DOCUMENTS

| | | |
|---|---|---|
| 41-21756 | 12/1941 | Japan . |
| 42-3074 | 2/1942 | Japan . |
| 42-8918 | 4/1942 | Japan . |
| 56-160998 | 12/1981 | Japan . |
| 2-27980 | 1/1990 | Japan . |

OTHER PUBLICATIONS

ATCC Catalogue of Bactoria and Phyos, 18th Edition, (1992), p. 293.
Ploux et al., (1992), Biochem. J., 287, 685–690.
Senoo et al., (1992), FEMS Microbiology Ecology, 86, 311–320.
Lobos et al., (1992), Appl. Microbiol Biotechnol, 37, 411–415.
Schmidt et al., (1992), FEMS Microbiology Letters, 96, 253–258.
Ohsugi et al., (1981), Agric. Biol. Chem., 47, 2725–2730.
Ogata et al., Agr. Biol. Chem., vol. 29, No. 10, pp. 889–894 (1965).
Izumi et al., Agric. Biol. Chem., vol. 45, No. 9, pp. 1983–1989 (1981).
Yabuuchi et al., Microbiol. Immunol., vol. 34 (2), pp. 99–119 (1990).
Akihiko Maruyama et al., Enzymatic Production of Ascorbic Acid-2-phosphate, Agric. Biol. Chem., 54 (9), pp. 2309–2313, 1990.

*Primary Examiner*—Marion C. Knode
*Assistant Examiner*—Kristin Larson
*Attorney, Agent, or Firm*—Birch, Stewart, Kolasch & Birch

[57] ABSTRACT

There is disclosed a process for the production of biotin, in which a culture of a microorganism of the genus Sphingomonas, having an ability to produce biotin, is prepared in a medium, and biotin produced and accumulated in the medium is collected. Also disclosed are microorganisms of the genus Sphingomonas, having an ability to produce biotin, which are useful for this production process of the present invention.

4 Claims, No Drawings ial scale.

PROCESS FOR PRODUCTION OF BIOTIN USING BACTERIA BELONGING TO THE GENUS SPHINGOMONAS

FIELD OF THE INVENTION

The present invention relates to a process for the production of biotin and microorganisms for use in this process.

BACKGROUND OF THE INVENTION

Biotin is one of the vitamins required for human beings, animals, vegetables and certain kinds of microorganisms. As a process for the production of biotin using a microorganism, there have heretofore been known various processes using a microorganism such as those of the genus Streptomyces or Micromonospore (JP-B 41-21756); Sporobolomyces (JP-B 42-3074); Bacillus (JP-A 56-160998); Escherichia (JP-A 61-149091); Serratia (JP-A 2-27980); and Brevibacterium (JP-A 3-240489).

These conventional processes are, however, not always satisfactory because of their low yield of biotin produced by any such microorganism. It is, therefore, required to develop a process for the production of biotin using a microorganism with higher efficiency, which is suitable for the biotin production on an industrial scale.

SUMMARY OF THE INVENTION

Under these circumstances, the present inventors have intensively sought microorganisms having an increased ability to produce biotin over the nature and various type culture collections maintained in the facilities for deposition of microorganisms. As the result, they found that microorganisms of the genus Sphingomonas can accumulate very large amounts of biotin into the medium, thereby completing the present invention.

Thus, the present invention provides a process for the production of biotin, characterized in that a microorganism of the genus Sphingomonas, having an ability to produce biotin, is cultured in an appropriate medium and biotin accumulated into the medium is collected. Also provided are microorganisms for use in this process.

DETAILED DESCRIPTION OF THE INVENTION

The microorganisms for use in the process of the present invention are those of the genus Sphingomonas, having an ability to produce biotin, examples of which are *Sphingomonas adhaeshiva*, *Sphingomonas parapaucimobilis* and *Sphingomonas paucimonilis*. Among these microorganisms, preferred is Sphingomonas sp. SC-42405. In general, the microorganisms of the genus Sphingomonas have, for example, the following characteristics:

(1) They are gram-negative rods;
(2) They exhibit positive in catalase test;
(3) Yellow colonies are mainly formed;
(4) They contain sphingolipids as phospholipids;
(5) Isoprenoid quinone type is Q10;
(6) They contain 2-hydroxy acids as bacterial fatty acids; and
(7) The mol % G+C of their DNA ranges from about 60–70.

Sphingomonas sp. SC-42405 is a microorganism which was isolated from the bacteria separated from the soil of Oita Prefecture, Japan, by the present inventors, and which was found to accumulate very large amounts of biotin in the medium. This microorganism has been deposited with the Fermentation Research Institute (renamed "National Institute of Bioscience and Human Technology") in the agency of Industrial Science and Technology, under the accession number of FERM BP-3995 on Sep. 3, 1992, under the Budapest Treaty.

The bacteriological characteristics of Sphingomonas sp. SC-42405 are as follows.

(a) Morphology:
  1. Shape and size of cells
    Shape: rods
    Size: 0.4–0.8 $\mu$m × 1.5–3.0 $\mu$m
  2. Polymorphism: none
  3. Motility: active, polar and peritrichous flagella
  4. Sporulation: none
  5. Gram staining: negative
  6. Acid fastness: none (b) Growth properties:
  1. Nutrient agar plate culture: round, convex, yellow
  2. Nutrient agar slant culture: smooth surface, slightly glossy, yellow
  3. Nutrient broth liquid culture: turbid growth
  4. Nutrient broth gelatin stab culture: not liquefied
  5. Litmus milk: not changed (c) Physiological properties:
  1. Nitrate reduction nutrient broth nitrate medium): —
  2. Denitrification: —
  3. MR test: —
  4. VP test: —
  5. Indole formation: —
  6. hydrogen sulfide formation: +
  7. Starch hydrolysis: —
  8. Citrate utilization
    Koser medium: +
    Christensen medium: +
  9. Inorganic nitrogen source utilization
    ammonium salts: +
    nitrates: +
  10. Pigment formation
    Cellular pigments: +(yellow)
    Water-soluble pigments (King's A medium): —
    Water-soluble pigments (King's B medium): —
  11. Urease: ±
  12. Oxidase: +
  13. Catalase: +
  14. Growth conditions
    pH: 5.1–7.9
    Temp.: 10°–33° C.
  15. Attitude to oxygen: slightly aerobic
  16. 0-F test: F (weak)
  17. Acid and gas formation from sugar

|  | Acid | Gas |
|---|---|---|
| (1) L-Arabinose: | + | — |
| (2) D-Xylose: | + | — |
| (3) D-Glucose: | ± | — |
| (4) D-Mannose: | ± | — |
| (5) D-Fructose: | + | — |
| (6) D-Galactose: | + | — |
| (7) Maltose: | ± | — |
| (8) Sucrose: | ± | — |
| (9) Lactose: | ± | — |
| (10) Trehalose: | — | — |
| (11) D-Sorbitol: | — | — |

-continued

|  | Acid | Gas |
|---|---|---|
| (12) D-Mannitol: | — | — |
| (13) Inositol: | — | — |
| (14) Glycerol: | — | — |
| (15) Starch: | ± | — |

(d) Other properties:

1. Aesculin hydrolysis: +
2. Arginine hydrolysis: —
3. Lysine decarboxylation: —
4. Ornithine decarboxylation: —
5. DNase: —
6. Tween 80 hydrolysis: —
7. 0/129 Sensitivity: —
8. Nitrogenase: —
9. Poly-β-hydroxybutyrate accumulation: +
10. Mol % G+C of DNA: 64.8
11. Molecular type of isoprenoid quinone: ubiquinone Q10
12. Sphingophospholipids: +
13. Composition of total bacterial fatty acids: C16:0 (13.1%), C16:1 (11.2%), C17:1 (1.1%), C18:1 (51.8%), 2-OH-14:0 (14.1%) and 2-OH-16:0 (4.5%)

The above-described properties in the item (d), 10–13, can be determined by conventional chemotaxomonical procedures such as described in "Experiments for Identification of Actinomycetes", edited by the Japanese Society for the Research of Actinomycetes and published by the Secretariat of the Japanese Society for the Research of Actinomycetes in 1985. Typical examples of such procedures will be explained below.

1. Mol % G +C of DNA

---

Culture (100 mL nutrient broth medium in Sakaguchi's flask at 30° C. for 36 hrs.)
  | ... Collect bacterial cells by centrifugation.
Wash twice by centrifugation with saline-EDTA (0.15 M NaCl, 0.1 M EDTA, 8.0).
  | ... Suspend bacterial cells in 18 mL of saline-EDTA.
Lysis of bacterial cells [lysozyme treatment (0.5 mg/mL at 37° C. for 1 hr.),
followed by addition of SDS (to final conc. of 12%) and heating at 60° C. for 15 min.]
  | ... Mixture becomes transparent and has increased viscosity by DNA.
  | ... Ice cooling
Add EtOH to final conc. of 67%.
  | ... Discard supernatant.
Dissolve in 20 mL of SSC (0.15 M NaCl, 0.015 M Na$_3$ citrate, pH 7.0).

Add phenol at equivalent volume to SSC (SSC saturation) and shake in stoppered flask.
  | ... Centrifuge (separation into three layers, i.e., water layer, natured protein layer and organic solvent layer).
Pipette out water layer.
  | ... Add SSC, followed by shaking again, centrifugation and removal of water layer.
  | ... Ice cooling
  | ... Centrifuge at 12,000 rpm for 10 min. at 4° C., and pour supernatant into beaker so as to have 1 cm thickness.
Winding of DNA
  | ... Add cold 95% EtOH at twice volume to water, while stirring the content of beaker with glass rod. At the conc. of about 30% EtOH, DNA begins to wind around glass rod. Let DNA winding around glass rod stand for a while in test tube containing 80% EtOH (removal of phenol), followed by the same treatment in 95% EtOH. Evaporate EtOH in air and put DNA into 0.1 × SSC. After standing in refrigerator overnight, substantially uniform solution is obtained.
  | ... Mildly centrifuge to remove turbidity.
RNase treatment (add RNase A* to 50 μg/mL and treat at 37° C. for 1 hr.)
  | * 1–2 mg/mL SSC is treated at 80° C. for 10 min (Deactivation of DNase).
  | ... Add 10 × SSC at 1/10 volume and cool.
Winding of DNA around glass rod while adding EtOH (if pure DNA, it becomes transparent)
  | ... Put into 0.1 × SSC and let stand in refrigerator overnight (if still turbid next day, repeat centrifugation, RNase treatment and winding).
  | ... Let A260 to be 10–20.
Put 100 μL of purified DNA/0.1 × SSC solution into microcentrifugation tube.
  | ... Maintain at 100° C. for 5 min., followed by ice cooling.
  | ← 100 μL of 0.1 mg/mL Nuclease P1 (Yamasa Shoyu, Co., Ltd.), 40 mM NaAc and 2 mM ZnSO$_4$ (pH 5.3)
Reaction at 50° C. for 1 hr.
  | ← 100 μL of Alkaliphosphatase (BAP, Takara Shuzo, Co., Ltd.) (2.4 U/mL in 0.1 M Tris-HCl, pH 8.1)
Reaction at 37° C. for 1 hr.

---

HPLC analysis
Column: Gμ C18+μBondasphere C18 (3.9 mmφ×150 mm),
Mobile phase: 0.2M NH$_4$H$_2$PO$_4$/MeOH (100:8),
Flow rate: 0.9 mL/min.,
Detection: UV 260 nm,
Sample injection: 5 μL (4–7 μL).

2. Molecular kind of isoprenoid quinone

---

100 mg of lyophilized bacterial cells (prepared as liquid culture in nutrient broth)
  | ... Extract overnight with 20 mL of CHCl$_3$—MeOH (2:1) under stirring.
Silica gel TLC analysis
  | ... Develop with benzene and determine which it is ubiquinone or menaquinone (when developed with benzene, if Rf = 0.3, it is ubiquinone, and if Rf = 0.7, it -continued is menaquinone).
Scrape off in silica gel TLC and purification
| Ubiquinone is developed with benzene, whereas mena-
  quinone is
| developed with n-hexane-benzene-CHCl$_3$ (5:2:1).
Remove by elution from silica gel with acetone
| ... Make 100 μl of acetone solution.
Reverse phase HPLC analysis
  Column: YMC-Pack AM-303 (4.6 mmφ × 250 mm),
  Elute: 2-PrOH—MeOH (25:75),
  Flow rate: 1.0 mL/min.,
  Detection: 270 nm.

3. Presence of sphingophospholipids 0.5 g of wet bacterial cells
| ... Extract phospholipids with 5 mL of CHCl$_3$—MeOH (2:1).
Separate CHCl$_3$ layer into two parts and add 88 μL of 6N KOH.
| ... Hydrolyze at 40° C. for 1 hr.
| ... Neutralize with acetic acid.
| ... Dry up.
TLC analysis (after development, color development is caused with molybdenum reagent.)

4. Composition of total bacterial fatty acids
(1) Procedures for analysis of total bacterial fatty acids 25 mg of lyophilized bacterial cells (prepared as liquid culture in nutrient broth at 30° C.)
|
| ← 2 mL of 5% anhydrous HCl—MeOH (Wako Pure
|   Chemical Industries, Ltd.)
| ... Maintain in boiling water for 3 hr.
Let stand for cooling.
| ← 1 mL of water
| ← 3 mL of n-hexane
Extract fatty acid methyl esters (shaking for 10 min.).
| ... Pipette out n-hexane layer.
| ... Add 3 mL of water and shake (acid removal).
| ... Remove n-hexane layer and dehydrate with anhydrous
  Na$_2$SO$_4$.
| ... Dry up.
Dissolve in 200 μL of CH$_3$CN.
|

Gas chromatography analysis
Column: 10% DEGS Chromosorb W 80/100 (AW-DMCS), 3 mmφ × 5.2 m,
Carrier: N$_2$ at 40 mL/min.,
Injection temp.: 220° C.,
Column temp.: 180° C.,
Detection: FID.
(2) Procedures for identification of unsaturated fatty acid methyl esters 20 μL of total bacterial fatty acid methyl ester sample
| ... Dry up.
Dissolve in 200 μL of ethyl ether.
| ← Add 5 μL of 2% Br$_2$ in ethyl ether.
| ... Put stopper and let stand at room temperature for 30 min.
Evaporate solvent and remaining Br$_2$ by blowing N$_2$ gas.
| ... Dissolve in 60 μL of CH$_3$CN.
Gas chromatography analysis [in the same manner as described in item (1)]

(3) Procedures for identification of hydroxy fatty acid methyl esters

20 μL of total bacterial fatty acid methyl ester sample

| ... Apply to silica gel TLC.
Development (n-hexane-ethyl ether, 85:15)
| ... Spray 0.02% (w/v) 2′,7′-dichlorofluorescein-ethanol
  solution.
Scrape off color-developed spots.
| If Rf = 0.2, the spot is 3-hydroxy fatty acid methyl ester.
| If Rf = 0.3, the spot is 2-hydroxy fatty acid methyl ester.
| If Rf = 0.8, the spot is non-polar fatty acid methyl ester.
Extract with ethyl ether, followed by dry up and dissolution in
  20 μL of CH$_3$CN.
|
Gas chromatography [in the same manner as described in item (1)]

(4) Procedures for identification of cyclo fatty acid methyl esters

20 μL of total bacterial fatty acid methyl ester sample
| ... Dry up.
Heat in 2 mL of 5% anhydrous HCl—MEOH at 100° C. for 1 hr.
|
Extract fatty acid methyl esters in the same manner as described
  in item (1) and dissolve in 20 μL of CH$_3$CN.
|
Gas chromatography analysis [in the same manner as described
in item (1)]

The above-described characteristics were compared with the data disclosed in "Bergey's Manual of Systematic Bacteriology" (1984), Yabuuchi et al., Microbiol. Immunol., 34, 99–119 (1990), Validation list No. 34, Int. J. Syst. Bacteriol., 40, 320–321 (1990), and the bacterial strain found by the present inventors was identified as a microorganism of the genus Sphingomonas and named Sphingomonas sp. SC-42405. It should be noted that them has not yet been known any microorganism of the genus Sphingomonas, having an ability to produce biotin. In this respect, Sphingomonas sp. SC-42405 is considered to be a novel strain. In addition, any variant of this strain, i.e., any mutant derived from Sphingomonas sp. SC-42405, any cell fusion strain or any recombinant strain is also available for the process of the present invention.

A culture of the microorganism for use in the process of the present invention can be prepared in various kinds of media containing carbon and nitrogen sources, organic and/or inorganic salts, and the like, all of which have been widely used for preparing a culture of ordinary bacteria.

Examples of the carbon sources are glucose, maltose, glycerol, starch, dextrin, sucrose, animal and vegetable oils, and molasses.

Examples of the nitrogen source are natural organic nitrogen sources such as broth, peptone, yeast extract, malt extract, soy bean powder, corn steep liquor, cotton seed powder, dry yeast and casamino acid; and other organic or inorganic nitrogen sources such as ammonia, ammonium chloride, sodium nitrate, ammonium nitrate, ammonium sulfate, ammonium acetate and urea. The natural organic nitrogen sources may also be utilized as a carbon source.

Examples of the organic and inorganic salts are chlorides, sulfates, acetates, carbonates and phosphates of elements such as potassium, sodium, magnesium, iron, manganese, cobalt and zinc. Specific examples thereof are potassium chloride, sodium chloride, magnesium sulfate, ferrous sulfate, manganese sulfate, cobalt chloride, zinc sulfate, copper sulfate, sodium acetate, calcium carbonate, sodium carbonate, potassium monohydrogenphosphate, potassium dihydrogenphosphate, sodium monohydrogenphosphate and sodium dihydrogenphosphate.

The microorganism for use in the process of the present invention has a superior ability to produce biotin in various media which are favorable for the production on an industrial scale. To increase the ability to produce biotin for the microorganism used in the process of the present invention, an amino acid such as alanine or a fatty acid such as pimelic acid may be added to the culture medium. For example, these compounds may be used at an amount of from about 1 mg to about 5 mg per 1000 mL of the culture medium.

A culture of the microorganism for use in the process of the present invention is prepared according to conventional procedures employed for ordinary bacteria, in the form of either a solid culture or a liquid culture such as shaking culture using test tubes, reciprocating shakers or rotary shakers, and other cultures using jar fermenters or fermentation tanks.

A culture of the microorganism is usually incubated under aerobic conditions. In particular, when a jar fermenter or a fermentation tank is used, it is necessary to introduce aseptic air thereinto, usually at a rate of from about 0.1 to about 2 times the culture volume per minute.

The incubation temperature may vary within a range in which the microorganism used is viable in culture. For example, the culture is incubated at a temperature of from about 20° C. to about 40° C., preferably from about 25° C. to about 35° C., and more preferably from about 28° to about 33° C. Preferably, the medium pH is controlled at from about 6 to about 8.

The incubation period may vary depending upon various conditions, and the culture is usually incubated over a period of from about 1 to about 7 days, preferably from about 3 to about 4 days.

After completion of the incubation, biotin is collected from the culture by making use of the properties of biotin according to conventional procedures for extraction and purification of a desired compound from natural sources. For example, the bacterial cells are removed from the culture by a technique such as centrifugation, and biotin accumulated in the culture is adsorbed on activated charcoal or a macro-porous non-ionic exchange resin, followed by purification with an ion exchange resin or recrystallization utilizing a difference of solubility between biotin and impurities.

The present invention will be further illustrated by way of the following examples which are not to be construed to limit the scope thereof.

EXAMPLE 1

Production of biotin by shaking culture

A loopful of Sphingomonas sp. SC-42405 (FERM BP-3995) was inoculated into a large test tube (22 mm$\phi \times$220 mm) containing 10 mL of pre-culture medium (1% glycerol, 2% polypeptone, 0.15% $K_2HPO_4$, 0.15% $MgSO_4.7H_2O$, pH 7.2), and incubated at 30° C. with shaking at 200 rpm for 3 days. Then, 2 mL of this pre-culture was inoculated into a 500 mL Sakaguchi's flask containing 50 mL of culture medium (2% glycerol, 2% yeast extract, 0.5% vitamin-free casamino acid, 0.15% $K_2HPO_4$, 0.05% KCl, 0.05% $MgSO_4.7H_2O$, 0.001% $FeSO_4.7H_2O$, 0.001% $MnSO_4.4-6H_2O$, 20 $\mu$g/L thiamine hydrochloride, pH 7.0), and incubated at 30° C. with shaking at 130 rpm for 4 days. The bacterial concentration ($OD_{650}$) after completion of the incubation was 22.0, at which time the concentration of biotin produced and accumulated in the medium was determined by quantitative microbial bioassay using Lactobacillus plantarum IFO 3070 (Izumi and Yamada, Methods of Vitaminological Experiments II, Water-soluble Vitamins, pp. 481-499, edited by the Vitaminological Society of Japan, Tokyo Kagaku Dohjin, 1985), and found to be 3.3 mg/L.

EXAMPLE 2

Production of biotin by aerobic stirring culture

A culture of Sphingomonas sp. SC-42405 in a large test tube was pre-incubated in the same manner as described in Example 1. The pre-culture was inoculated as 2 mL portions into three 500 mL Sakaguchi's flasks each containing 100 mL of the same pre-culture medium, and incubated at 30° C. with shaking at 130 rpm for 3 days. Then, 300 mL of this culture was inoculated into a 30 L jar fermenter containing 15 L of culture medium (2% glycerol, 2% yeast extract, 0.5% vitamin-free casamino acid, 0.15% $K_2HPO_4$, 0.05% KCl, 0.05% $MgSO_4.7H_2O$, 0.001% $FeSO_4.7H_2O$, 0.001% $MnSO_4.4-6H_2O$, 20 $\mu$g/L thiamine hydrochloride, pH 7.0), and incubated at 30° C. with aeration and stirring for 4 days. The rate of aeration was 15 L/min., and the rate of stirring was from 200 to 500 rpm (controlled so that the concentration of dissolved oxygen in the medium became 2 ppm or higher). The self-defoaming was achieved by addition of defoamer Einol (Biotto Co.). The bacterial concentration ($OD_{650}$) after completion of the incubation was 38.0, at which time the concentration of biotin produced and accumulated in the medium was determined by the same quantitative microbial bioassay as described in Example 1, and found to be 2.3 mg/L.

EXAMPLE 3

Isolation and Identification of products

Fifteen liters of the culture obtained in Example 2 were subjected to continuous centrifugation, and after adjusted to pH 3 by addition of HCl, the supernatant was allowed to pass through a column packed with 500 g of activated carbon (Wako Pure Chemical Industries, Ltd.). The column was washed with 15 L of water, followed by elution with 5 L of 0.1N ammonia water. The eluate was concentrated and allowed to pass through a column packed with 100 mL of Dowex 1×8 (The Dow Chemical Co.), followed by washing with 2 L of water and elution with 2 L of 1N acetic acid. The eluate was concentrated and allowed to pass through a column packed with 100 mL of Dowex 50W-8 (The Dow Chemical Co.), followed by elution with 2 L of water. The eluate was concentrated and allowed to pass through a column packed with 50 g of activated carbon (Wako Pure Chemical Industries, Ltd.). The column was washed with 500 mL. of water, followed by elution with 500 mL of 0.1N ammonia water. The eluate was evaporated to dryness, and the residue was dissolved in 5 mL of 0.1N aqueous sodium hydroxide, followed by purification through gel filtration chromatography using a column packed with 50 mL of Sephadex G-10 (Pharmacia AB ). The fractions containing eluted biotin were combined and adjusted to pH 3 by addition of 0.05N HCl, after which the combined fractions were allowed to stand overnight in a cool place. The precipitated crystals were collected and dried under reduced pressure, resulting in 13 mg of biotin crystals. The thus obtained biotin exhibited the same physicochemical properties (e.g., mass spectrum, infrared absorption spectrum) as those of the standard preparation of biotin.

EXAMPLE 4

Comparison of biotin production between various microorganisms

A loopful of each of various microorganisms of the genus similar to the genus Sphingomonas was inoculated into a large test tube (22 mm$\phi$ × 220 mm) containing 5 mL of pre-culture medium (1% glycerol, 2% polypeptone, 0.15% $K_2HPO_4$, 0.15% $MgSO_4.7H_2O$, pH 7.2), and incubated at 30° C. with shaking at 250 rpm for 3 days. After completion of the incubation, the concentration of biotin produced and accumulated in the culture medium was determined by the same quantitative microbial bioassay as described in Example 1. The results are shown in Table 1.

TABLE I

| Microorganism | | Biotin production ($\mu$g/L) | Growth at 30° C. |
|---|---|---|---|
| Flavobacterium flavescens | JCM 7456 | trace | + |
| Flavobacterium okeanokoites | IFO 12536 | trace | + |
| Pseudomonas auricularis | IFO 13334 | trace | + |
| Pseudomonas bathycetes | JCM 6308 | trace | + |
| Pseudomonas chlororaphis | IFO 3904 | trace | + |
| Pseudomonas diminuta | JCM 2788 | trace | + |
| Pseudomonas fluorescens | IFO 14160 | trace | + |
| Pseudomonas fragi | IFO 3458 | trace | + |
| Pseudomonas mucidolens | JCM 2781 | trace | + |
| Pseudomonas nitroreducens | JCM 2782 | trace | + |
| Pseudomonas oxalaticus | IFO 13593 | trace | + |
| Pseudomonas pertucinogena | IFO 14163 | trace | + |
| Pseudomonas putida | IFO 14164 | trace | + |
| Pseudomonas riboflavina | IFO 13584 | trace | + |
| Pseudomonas straminea | JCM 2783 | trace | + |
| Pseudomonas vesicularis | JCM 1477 | trace | + |
| Pseudomonas fluorescens | | trace* | +* |
| Pseudomonas aeruginosa | | trace* | +* |
| Pseudomonas taetrolens | IFO 3460 | trace** | +** |
| Sphingomonas adhaeshiva | JCM 7370 | 2.3 | + |
| Sphingomonas parapaucimobilis | JCM 7512 | 3.1 | + |
| Sphingomonas paucimobilis | IFO 13935 | 9.8 | + |
| Sphingomonas paucimobilis | IFO 13936 | 6.4 | + |
| Sphingomonas paucimobilis | JCM 7509 | 5.8 | + |

TABLE I-continued

| Microorganism | | Biotin production ($\mu$g/L) | Growth at 30° C. |
|---|---|---|---|
| Sphingomonas paucimobilis | JCM 7511 | 12.4 | + |
| Sphingomonas paucimobilis | JCM 7515 | 13.7 | + |
| Sphingomonas paucimobilis | JCM 7519 | 15.5 | + |
| Sphingomonas paucimobilis | JCM 7521 | 9.5 | + |
| Sphingomonas sp. | JCM 7513 | 2.7 | + |
| Sphingomonas sp. | JCM 7514 | 4.2 | + |
| Sphingomonas sp. | SC-42405 (FERM BP-3995) | 17.4 | + |
| Xanthomonas campestris | IFO 13551 | — | — |
| Xanthomonas maltophilia | JCM 1975 | — | — |

*Data disclosed in Agr. Biol. Chem., 29, 10, 889–894 (1965).
**Data disclosed in Agr. Biol. Chem., 45, 9, 1983–1989 (1981).

What is claimed is:

1. A process for the production of biotin, comprising the steps of:
   (a) culturing a microorganism of the genus Sphingomonas in a nutrient medium under conditions to produce biotin, and
   (b) recovering said biotin accumulated,
   wherein said microorganism is selected from the group consisting of Sphingomonas sp. SC-42405 (FERM BP-3995) or a mutant thereof capable of producing biotin, Sphingomonas adhaeshiva JCM 7370, Sphingomonas parapaucimobilis JCM 7512, Sphingomonas paucimobilis IFO 13935, Sphingomonas paucimobilis IFO 13936, Sphingomonas paucimobilis JCM 7509, Sphingomonas paucimobilis JCM 7511, Sphingomonas paucimobilis JCM 7515, Sphingomonas paucimobilis JCM 7519, Sphingomonas paucimobilis JCM 7521, Sphingomonas sp. JCM 7513, and Sphingomonas sp. JCM 7514.

2. A biologically pure culture of Sphingomonas sp. SC-42405 (FERM BP-3995) or a mutant thereof capable of producing biotin.

3. The process according to claim 1, wherein the nutrient medium contains alanine in an amount of from about 1 mg to about 5 mg per 1000 ml of nutrient medium.

4. The process according to claim 1, wherein the nutrient medium contains pimelic acid in an amount of from about 1 mg to about 5 mg per 1000 ml of nutrient medium.

* * * * *